March 17, 1942. W. T. KIRKMAN, JR Plant Pat. 506

PEACH

Filed Oct. 12, 1940

WITNESS

Addison E. Avery

INVENTOR

Wm. T. Kirkman Jr.

BY Webster & Webster

ATTORNEYS

Patented Mar. 17, 1942

Plant Pat. 506

UNITED STATES PATENT OFFICE

506

PEACH

William T. Kirkman, Jr., Tracy, Calif., assignor to Kirkman Corporation, Tracy, Calif., a corporation of California Application October 12, 1940, Serial No. 360,940

1 Claim. (Cl. 47—62)

This discovery relates in general to a new and distinct variety of peach tree and its fruit, and more particularly to a variety of peach tree whose fruit is of the freestone type and possessed of novel and commercially advantageous characteristics.

This new variety is a bud mutation which occurred on a seven year old Rio Oso Gem growing in my orchard in Madera County, California; the discovery of such bud mutation having been made by me in the summer of 1937, and subsequently has been asexually reproduced. The new variety herein claimed is generally similar to the parent in tree growth, bloom and foliage, but as will subsequently appear in detail, is characterized by fruit having equal or better eating quality than the J. H. Hale, Elberta, or Rio Oso Gem varieties, but ripening much later than the same; a flesh which remains firm longer than average period after maturity; larger average size as compared to Rio Oso Gem variety; and outstanding color markings.

Figure 1:
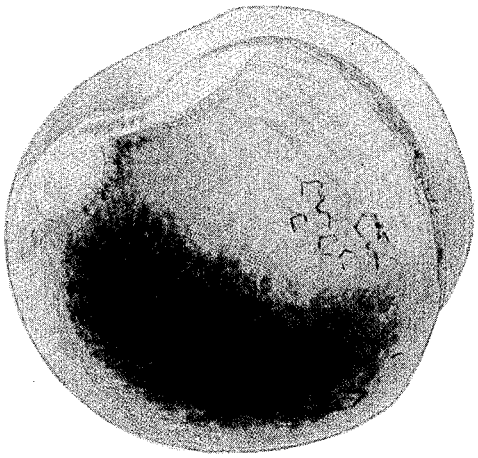

Figure 1 of the original drawing is a full size, perspective view, in natural color, of one of the peaches of the new variety.

Figure 2:
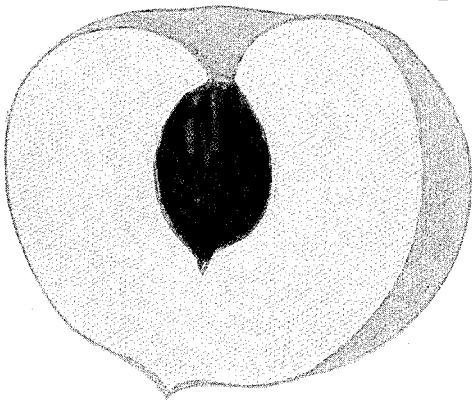

Figure 2 is a sectional elevation, in the suture plane of the peach shown in Fig. 1.

The following description sets forth in detail the characteristics of the peach tree and its fruit:

*Tree.*—The tree is of medium size and strength, spreading, open, and vase formed; being a productive and regular bearer. The trunk is stocky, as are the branches, the latter being brown in color. Lenticels are few and small.

*Leaves.*—The leaves are of medium size, averaging 6½″ in length and 1¼″ in width, acuminate, acutely pointed, medium thickness, dark green and smooth. The margin is crenate with minute reddish points. Petiole is medium to short. The glands are opposite, large, reniform, green, and average two to four in number, with several on petiole and on base of leaf.

*Flower buds and flowers.*—The flower buds are large and plump, and the flowers are of large size and pink in color as those of the parent variety, Rio Oso Gem.

*Fruit.*—To a certain extent color identification of the fruit has been made by direct comparison with Maerz and Paul dictionary of color, and indicia corresponding to plate letter and number respectively of said dictionary are set forth following color descriptions.

The fruit at maturity is of large size, averaging 3¼″ in axial diameter and 3⅜″ transversely in suture plane. The fruit is round-truncate in form, having a suture which is a relatively inconspicuous line, but particularly identified by a deep reddish streak about ¼″ wide which appears in advance of the balance of the coloring of the fruit. The suture extends from the base to beyond but discontinuous at the apex; there being a slight depression beyond the pistil point. The ventral surface is rounded slightly. The cavity is flaring, rounded, elongated in the suture plane with suture showing on one side, and averages ½″ to ⅝″ in depth and 1″ in breadth. The base is rounded, while the apex is short and depressed. The pistil point is slightly oblique. The skin is of medium thickness, tough, tenacious to the flesh, with no tendency to crack. Down is medium, short and does not roll up when rubbed. The skin is jasmine (9K4) in color and on the side exposed to the sun is overlain with a deep reddish color (5L3) shading into a relatively large or denser area of deep garnet (7J6); such area including a faint, irregular honeycomb of veins of a slightly darker shade (55L1). The skin on the opposite side of the suture and adjacent thereto is minutely stripped and spotted with Corinthian red (5J2).

The flesh of the fruit, in section, shades from a yellow (9H4) adjacent the base and on one side of the stone thereabout through a golden yellow (10L7) to a capucine yellow (9K8) on the opposite side.

The flesh of the fruit is streaked or rayed with a reddish shade (1G11) surrounding the stone and deepening (3L4) close thereto, and the surface of the pit cavity is red with yellow and pink fibers. Juice is moderate but rich. The texture of the flesh is firm and melting, with a few tender fibers, ripens evenly, and has a mildly acid flavor. The eating quality of the fruit is superior.

The stone is free, with short fibers; the average size of the stone being 1½″ in length, 1″ in breadth, and ¾″ in thickness. The stone is oval with oblique base, acuminate apex, sides equal and flattened, and the surface regularly furrowed toward the apex and pitted toward the base. The ridges are rounded and interrupted. Pits are elongated, and ventral edge thin with the wing throughout. Dorsal edge is narrow with shallow, narrow groove to above center. The color of the stone is rustic brown (7H11) tinged slightly with red.

*Ripening period.*—The fruit of the above described variety of peach ripens in mid-September in Madera County, California; the dates of first and last picking being about September 4 and September 20 respectively.

*Use.*—The fruit is of excellent shipping and eating quality, and in addition may be used successfully as a canning freestone.

As compared to Rio Oso Gem and similar varieties, my new variety is distinctively characterized by:

(*a*) Its late ripening period which, as indicated above, is about mid-September at Madera, California. This is approximately five weeks later than the Rio Oso Gem parent, and approximately six weeks later than the J. H. Hale and Elberta varieties. The fruit of the new variety furnishes a high quality freestone peach supply for the important market season following the exhaustion of fresh and satisfactory storage supplies of peaches such as those identified above. The picking and marketing period of this new variety is not covered by any other peach of comparable quality and attractiveness. All attempts to breed a late freestone peach of mid-summer quality have failed to eliminate, or satisfactorily replace, the poor and unpopular qualities of late variety breeding parents such as Salway, Piquetts Late, or Millers Late, which have exerted predominant quality influence in hybrid progeny.

(*b*) The flesh of the fruit remains firm an unusual length of time after it has attained a shipping or canning stage of maturity and sweetness;

(*c*) The average larger size of the fruit as compared to its Rio Oso Gem parent.

(*d*) Its outstanding color markings when ripe, including the suture identified by a deep red streak extending therealong.

The characteristics of my new variety of peach tree and its fruit as described above are of course typical, but may be subject to certain variations in detail as all varieties of fruit differ somewhat among themselves in adaptation to a particular region, soil or climatic conditions.

Having thus described my new variety of peach and its fruit, what I claim as new and useful and desire to secure by Letters Patent is:

The herein described variety of peach tree characterized by the average larger size of its freestone fruit and later ripening period thereof, the unusual length of time the flesh remains firm after maturity, and the outstanding color of its fruit including a deep reddish streak following the suture; all as compared to the Rio Oso Gem.

WILLIAM T. KIRKMAN, JR.